Figure 1:
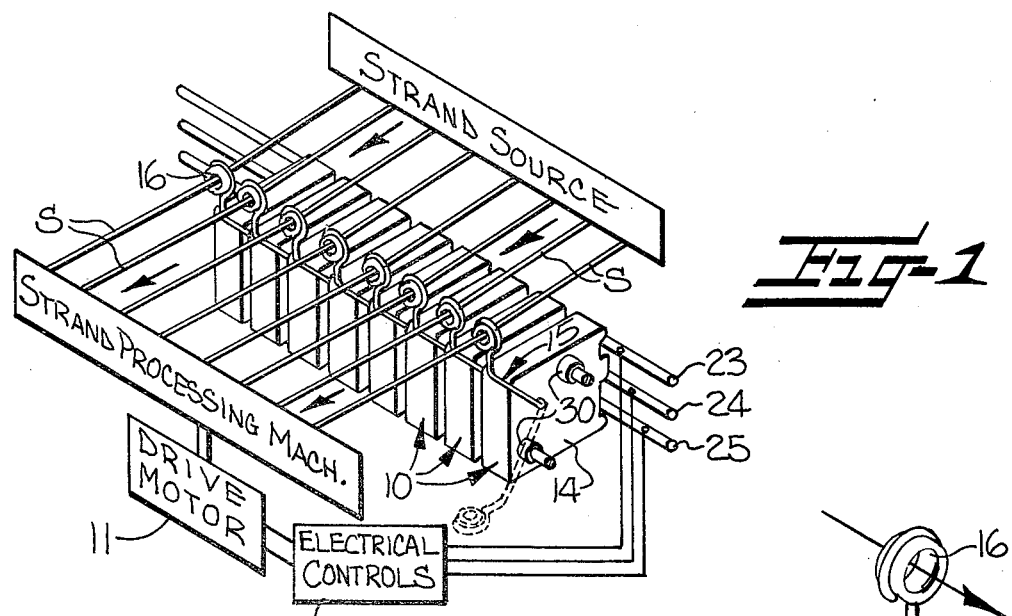

United States Patent [19]

White et al.

[11] 4,169,981
[45] Oct. 2, 1979

[54] STRAND RESPONSIVE ELECTRICAL SWITCH

[76] Inventors: Eugene F. White; Frances H. White, both of Rte. 4, Box 118, Monroe, N.C. 28110

[21] Appl. No.: 763,841

[22] Filed: Jan. 31, 1977

[51] Int. Cl.$^2$ ............................................. G01N 21/30
[52] U.S. Cl. ...................................... 250/561; 28/187; 250/229
[58] Field of Search .................. 250/561, 229; 28/187; 57/81; 66/161; 139/273 A

[56] References Cited

U.S. PATENT DOCUMENTS

| | | | |
|---|---|---|---|
| 2,233,483 | 3/1941 | Metcalf | 250/561 |
| 3,010,273 | 11/1961 | Bailey | 28/187 |
| 3,800,162 | 3/1974 | Lueck | 28/187 |

FOREIGN PATENT DOCUMENTS 1171755  1/1959  France ......................................... 28/51

Primary Examiner—David C. Nelms
Attorney, Agent, or Firm—Bell, Seltzer, Park & Gibson

[57] ABSTRACT

In combination with apparatus for advancing at least one individual tensioned textile strand along a predetermined path of travel, an electrical switch capable of signalling a need for stopping of the apparatus in response to the occurrence of an improper operating condition of an individual strand. The switch device has a housing for mounting adjacent the path of travel of a strand, a guide for engagement with the strand and for movement relative to the housing in response to strand conditions such as breakage or excessive slack, a light actuated electrical switch within the housing, a light source within the housing for illuminating the switch, and a shutter mounted for movement in response to movement of the guide and optically interposed between the switch and the light source for controlling the electrical signalling of the switch in response to occurrence of improper operating conditions.

10 Claims, 3 Drawing Figures

U.S. Patent

Oct. 2, 1979

4,169,981

STRAND RESPONSIVE ELECTRICAL SWITCH

Many processes of manufacture which rely upon the use of strand materials, and particularly certain textile manufacturing processes and apparatus as pointed out more fully hereinafter, rely upon the continued presence of strand materials in achieving acceptable and satisfactory performance. Particularly with textile apparatus or apparatus in which textile strands are used, it has become conventional to provide mechanism for sensing the presence and operating condition of advancing strands and for signalling any occurrence of an improper operating condition. Most such mechanisms provided heretofore have been mechanical or, at best, electro-mechanical. Such devices have been known, in certain applications in the textile industry, as "stop motions" and will be recognized by that name by many persons skilled in the arts to which the present invention is applicable.

Prior stop motions and similar devices of an electro-mechanical nature have conventionally relied upon physical contact switches. That is, switching of electrical circuits have been accomplished by the physical contact of a pair of conductors. The difficulties encountered with such electro-mechanical devices have been well-documented by the problems recognized in prior patents directed to such devices and typically relate to contamination of switch surfaces by foreign materials, wear, and risk of fire and other dangers from electrical arcing or the like.

With the above difficulties in mind, it is an object of the present invention to provide means for electrically signalling the occurrence of an improper operating condition of an advancing tensioned strand which is not subject to the problems and difficulties of the prior electro-mechanical devices and is thus readily adaptable to use in combination with a range of apparatus in which individual tensioned textile strands are advanced along respective predetermined paths of travel. In realizing this object of the present invention, reliance is placed upon the optical coupling of a light actuated switch and a light source, with a shutter being mounted for movement therebetween in response to occurrence of an improper operating condition of a corresponding strand.

Yet a further object of the present invention is to provide an electrical signalling means of the general type described which is particularly well adapted for mounting of a plurality of devices in a closely packed array for responding to the operating condition of a corresponding number of strands being advanced at the same time by a common apparatus. In realizing this object of the present invention, a contactless device is provided which is readily adapted for mounting and use in conjunction with apparatus handling large numbers of textile strands such as a beaming apparatus or a knitting machine.

Figure 2:
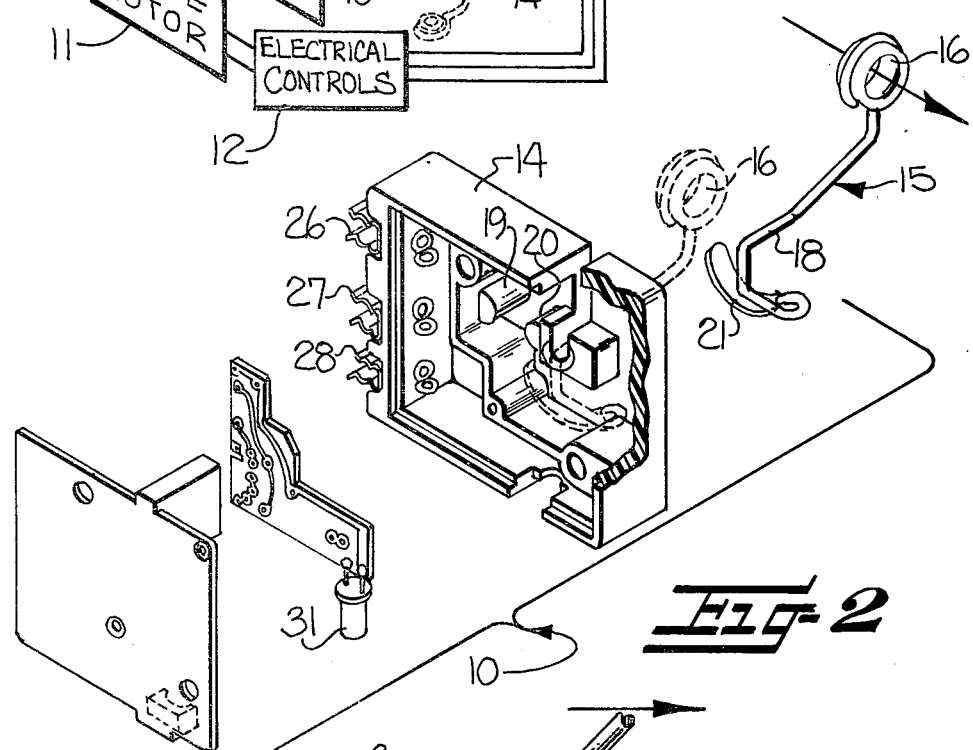
Figure 3:
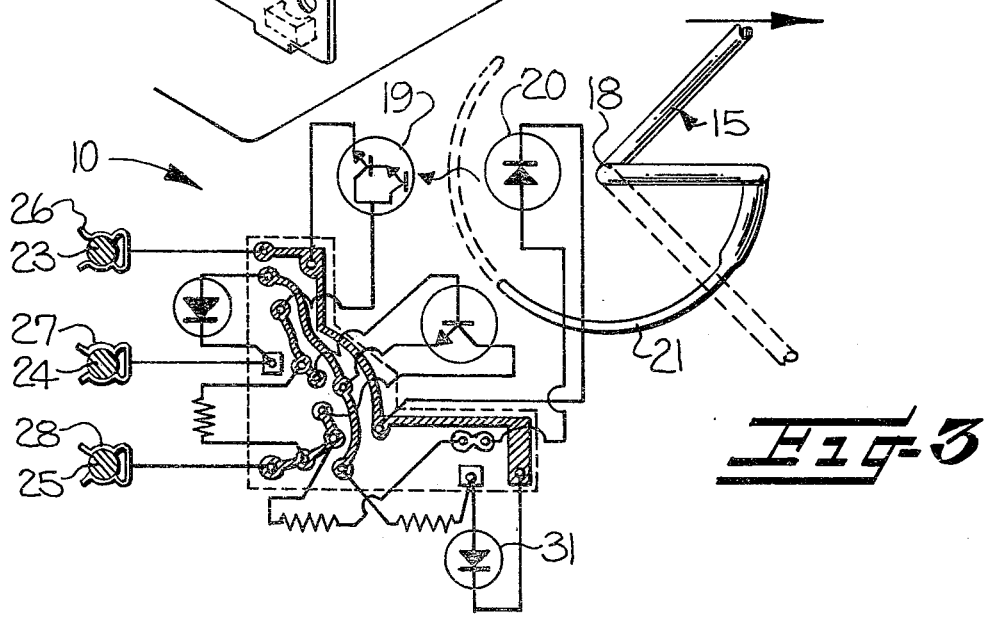

Some of the objects of the invention having been stated, other objects will appear as the description proceeds, when taken in connection with the accompanying drawings, in which FIG. 1 is a perspective view illustrating a number of devices in accordance with the present invention as mounted in an environment or use;

FIG. 2 is an exploded perspective view of one electrical signalling device in accordance with the present invention; and FIG. 3 is a schematic diagram of circuitry embodied in one form of device in accordance with this invention.

While this invention will be described hereinafter with particular reference to the accompanying drawings, it is to be understood at the outset of the following description that persons skilled in the applicable arts will be able to modify specific details of the arrangement of this invention while continuing to gain the benefit of the novel characteristics hereof. Accordingly, the following description and the accompanying drawings are to be understood as being a broad teaching of the present invention, and are not to be taken as being restrictive.

Referring now more particularly to FIG. 1, the electrical signalling means of the present invention, individual ones of which are respectively and generally indicated at 10, are shown in combination with apparatus for advancing an individual tensioned textile strand. As shown, the apparatus advances a plurality of such strands S each along a respective predetermined path of travel and for that purpose includes drive means generally indicated at 11 and an electrical control means generally indicated at 12 for stopping the drive means 11. Persons skilled in the applicable textile arts will recognize that the apparatus incorporating the drive means 11 and control means 12 may take a variety of forms including, by way of example and not by way of limitation, warp beam winding machines and knitting machines. Still other applications will be recognized by appropriately skilled persons from consideration of the description which follows.

In accordance with the present invention, each device 10 functions as a means for electrically signalling the occurrence of an improper operating condition of a corresponding advancing tensioned strand S. More particularly, the devices 10 signal, in the form illustrated, excessive slack or breakage or absence of the respective strands. As will be appreciated, the devices may also be arranged to signal an occurrence of an excessively taut or tensioned strand.

Each device 10 comprises a housing means 14 for mounting adjacent a corresponding predetermined path of strand travel. A guide means generally indicated at 15 is mounted from the housing means 14 for engagement with a strand and for movement relative to the housing in response to the occurrence of an improper operating condition of the engaged strand. The guide means 15 takes the form of an elongate member having an eyelet 16 at a free terminal end thereof and having a pivotal end portion 18 which penetrates the housing means 14 so as to be mounted therefrom for pivotal movement about a pivotal axis which extends transversely of the housing 14. As installed for use, the pivotal axis normally extends horizontally, as illustrated in FIG. 1. The eyelet 16 normally threadingly receives a corresponding textile strand S and is biased by gravity toward a dropped position. By the threading engagement of the strand with the eyelet 16, the elongate member forming the guide means 15 is held in a raised position, from which the guide means 15 drops in the event of breakage or run out of the strand or in the event of an excessive and unacceptable slackening.

Mounted within the housing 14 is a light actuated electrical switching means generally indicated at 19. Preferably, and as shown in FIG. 3, the switching means 19 is a light actuated transistor. Also mounted within the housing 14 is a light source means 20 for illuminating the switching means 19. Preferably, and as illustrated in the schematic diagram of FIG. 3, the light source means is a light emitting diode. The light actuated transistor and light emitting diode are optically coupled within the housing so that the light source means 20 illuminates the switching means 19 and thus controls the conductive state thereof. The housing 14 serves to preclude other illumination of the switching means 19.

A shutter means 21 is also mounted within the housing 14 for movement in response to movement of the guide means 15 and is optically interposed between the switching means 19 and the light source 20. As will be appreciated, movement of the shutter means 21 controls reception at the light actuated transistor of light emitted from the light emitting diode and thereby controls the electrical signal output from the device 10. As will be appreciated, the shutter means 21 is mechanically attached to or formed integrally with the pivotal end portion 18 of the guide means 15 and thereby moves in response to the operating condition of the corresponding tensioned strand.

In order to facilitate the mounting of a plurality of the devices 10 in an array adjacent the paths of travel of the corresponding strands, as illustrated in FIG. 1, a plurality of elongate bus conductor mounting rod means 23, 24, 25 are provided and are positioned to extend transversely of the predetermined paths of the strands S. Each housing 14 carries a corresponding plurality of conductive mounting clip means 26, 27, 28 for mounting the corresponding housing from the rod means 23, 24, 25. The clips 26, 27, 28 are electrically connected with circuitry within the housing 14 and function for conducting electrical currents between corresponding ones of the rod means 23, 24, 25 and the circuitry within the housing including the switching means 19 and the light source means 20. As will be appreciated, the rods 23, 24, 25 and clips 26, 27, 28 facilitate ready interchangeability of the devices 10. As shown, the relative spacing among the rods is such as to restrict insertion of any given housing 14 into an array in only one operative position, thereby assuring that improper electrical connections are avoided. As will be appreciated by persons skilled in the applicable arts, one of the rods, 23, 24, 25 may function as a common or ground, with another functioning as a voltage source and the third functioning as a signal conductor. By means of the latter rod, stop signals may be routed to the control 12 for stopping the apparatus drive 11.

In order to accommodate free movement of the guides 15 of the plurality of adjacent devices 10, each housing 14 has spacing projection means 30 extending therefrom for engaging an adjacent housing. By such engagement of adjacent housings, the housings are spaced one from the other by at least a predetermined distance less than the lateral projection of a guide 15 from its corresponding housing. Additionally, each housing 14 is penetrated at the location of the projections 30 by mounting openings, in order that an array of devices 10 may be joined together by elongate bolts penetrating the mounting openings.

Operators familiar with apparatus of the type illustrated in FIG. 1 will be able to appreciate the difficulty of identifying a particular strand which is in an improper operating condition upon stoppage of the apparatus. In accordance with the present invention, such identification of a controlling strand is facilitated by signal light means 31 mounted on each of the housings 14 and responsive to the corresponding switching means 19 therewithin for attracting the attention of an operator to the correspondingly improperly conditioned strand.

In the drawings and specification, there has been set forth a preferred embodiment of the invention, and although specific terms are employed, they are used in a generic and descriptive sense only and not for purposes of limitation.

That which is claimed is:

1. In combination with apparatus for advancing an individual tensioned textile strand along a predetermined path of travel, means for electrically signalling the occurrence of an improper operating condition of the advancing tensioned strand and comprising housing means defining a relatively thin and flat generally rectilinear package for mounting adjacent said path, guide means mounted from said housing means for engagement with said strand and for pivotal movement relative to said housing means about an axis extending transversely of said housing means in the direction of the thin dimension of said package and in response to said occurrence, light actuated electrical switching means within said housing means for electrically signalling the occurrence of a change in the illumination thereof, light source means within said housing means for illuminating said switching means, shutter means mounted within said housing means for movement in response to movement of said guide means and optically interposed between said switching means and said light source means for controlling the electrical signalling of said switching means in response to said occurrence, and means positioned on an edge of said package for mounting said housing means in operative position.

2. Apparatus according to claim 1 wherein said guide means comprises an elongate member having a pivotal end portion mounted from said housing for pivoting relative thereto and eyelet means at the end of said elongate member remote from said pivotal end for threadingly receiving said strand.

3. Apparatus according to claim 2 wherein said elongate member is mounted for pivotal movement about a horizontal pivotal axis and is biased by gravity toward a dropped position, said elongate member being adapted to be held in a raised position by engagement of said eyelet means with the tensioned strand, and said switching means and said shutter means cooperating for electrically signalling in response to one of slackening and breakage of the tensioned strand.

4. Apparatus according to claim 2 wherein said shutter means is fixed to said pivotal end portion of said elongate member for movement therewith relative to said housing.

5. Apparatus according to claim 1 wherein said switching means comprises a light actuated transistor and said light source means comprises a light emitting diode optically coupled with said transistor.

6. In combination with apparatus for advancing a plurality of individual tensioned textile strands along respective predetermined paths of travel, means for electrically signalling the occurrence of an improper operating condition of one of the advancing tensioned strands and comprising a plurality of devices corresponding to the number of strands with each said device comprising housing means defining a relatively thin and flat generally rectilinear package, guide means mounted from said housing means for engagement with a corresponding one of said strands and for pivotal movement relative to said housing means about a generally horizontal axis transversely of said housing means in the direction of the thin dimension of said package and in response to an improper operating condition of said corresponding one strand, light actuated electrical switching means within said housing means for electrically signalling the occurrence of illumination thereof, light source means within said housing means for illuminating said switching means, and shutter means mounted within said housing means for movement in response to movement of said guide means and optically interposed between said switching means and said light source means for controlling the electrical signalling of said switching means in response to said occurrence; and said electrical signalling means further comprising means for mounting said plurality of devices in a stacked array adjacent said paths of travel and with said axes of said guide means substantially aligned.

7. Apparatus according to claim 6 wherein said means for mounting said plurality of devices comprises a plurality of elongate buss conductor mounting rod means extending transversely of said predetermined paths and further comprising a corresponding plurality of conductive mounting clip means secured to each said housing means at an edge of said package for mounting the same from said rod means and for conducting electrical currents between said rod means and said switching means and said light source means, said rod means and said clip means facilitating ready interchangeability of said electrical signalling means.

8. Apparatus according to claim 7 and further comprising spacing projection means extending from each said housing means for engaging an adjacent housing and for spacing adjacent housing means one from the other by at least a predetermined distance, said projection means and said guide means cooperating for assuring freedom of movement of individual ones of said guide means without interference with an adjacent one of said electrical signalling means.

9. Apparatus according to claim 6 and further comprising signal light means mounted on each said housing means and responsive to the corresponding one of said switching means for attracting the attention of an operator to the corresponding improperly conditioned strand.

10. In combination with apparatus having drive means for advancing a plurality of individual textile strands along respective predetermined paths of travel and electrical control means for stopping said drive means, means for electrically signalling the occurrence of an improper operating condition of one of the advancing tensioned strands and comprising a plurality of devices corresponding in number to the number of strands with each said device comprising housing means for mounting adjacent a corresponding one of said paths, guide means mounted from said housing means for engagement with a corresponding one of said strands and for movement relative to said housing means in response to an improper operating condition thereof, light actuated electrical switching means within said housing means for electrically signalling the occurrence of illumination thereof and electrically connected with said control means for controllably stopping said drive means, light source means within said housing means for illuminating said switching means, and shutter means mounted within said housing means for movement in response to movement of said guide means and optically interposed between said switching means and said light source means for controlling the electrical signalling of said switching means and the stopping of said drive means in response to said occurrence.

* * * * *